United States Patent [19]

Cormier et al.

[11] 4,299,728
[45] Nov. 10, 1981

[54] BLOOD GAS CONTROL

[75] Inventors: Alan D. Cormier, Newburyport; Marvin Feil, Brookline; Kenneth D. Legg, Wellesley, all of Mass.

[73] Assignee: Instrumentation Laboratory Inc., Lexington, Mass.

[21] Appl. No.: 170,600

[22] Filed: Jul. 21, 1980

[51] Int. Cl.$^3$ .................. C09K 3/00; G01N 33/48; B01J 13/00; G01N 33/00

[52] U.S. Cl. .................. 252/408; 23/230 B; 23/232 R; 252/312; 424/325; 424/339; 424/342; 424/350; 424/352

[58] Field of Search ............ 252/312, 408; 23/230 B, 23/232 R; 424/352, 339, 342, 350, 325

[56] References Cited

U.S. PATENT DOCUMENTS

| | | | |
|---|---|---|---|
| 3,629,142 | 12/1971 | Marbach | 252/408 |
| 3,681,255 | 8/1972 | Wilfore | 252/408 |
| 3,778,381 | 12/1973 | Rosano et al. | 252/312 |
| 3,823,091 | 7/1974 | Samejima et al. | 252/312 |
| 3,911,138 | 10/1975 | Clark, Jr. | 424/352 |
| 3,973,913 | 8/1976 | Louderback | 252/408 |
| 3,993,581 | 11/1976 | Yokoyama et al. | 252/312 |
| 4,001,142 | 1/1977 | Turner | 252/408 |
| 4,116,336 | 9/1978 | Sørensen et al. | 252/408 |
| 4,151,108 | 4/1979 | Sørensen et al. | 252/408 |
| 4,163,734 | 8/1979 | Sørensen et al. | 252/408 |

FOREIGN PATENT DOCUMENTS 1343870 1/1974 United Kingdom .............. 252/408

OTHER PUBLICATIONS

Mass, A. H. J., et al., Clin. Chem, vol. 23, No. 9, pp. 1718-1725, (1977).
Clark, Jr.; et al., Ala. J. Med. Sci., vol. 9, No. 1, pp. 16-29, (1972).
"The Merck Index", 8th ed., Merck & Co., Inc., Rahway, N. J., p. 469, (1968).

Primary Examiner—Teddy S. Gron

[57] ABSTRACT

A blood gas control liquid comprises water, 5-40 percent by volume of a water-insoluble perfluorinated compound material that has an oxygen solubility coefficient, at one atmosphere pressure, 25° C., and a volumetric proportion of 15 percent of at least 10 ml $O_2$ per 100 mL emulsion, 0.25-10 percent by volume of a nonionic, fluorocarbon-based surfactant, a preservative agent and a buffering agent which is substantially non-reactive with said preservative agent. The blood gas control liquid has a pH in the range of 7-8, a partial pressure of carbon dioxide in the range of 15-80 millimeters Hg, and a partial pressure of oxygen in the range of 20-600 mm Hg.

10 Claims, No Drawings

BLOOD GAS CONTROL

This invention relates to blood gas control liquids for quality control and/or calibration of blood gas analyzer equipment.

Blood gas analyzers are utilized to measure parameters of blood such as pH, partial pressure of carbon dioxide (expressed as $pCO_2$), and partial pressure of oxygen (expressed as $pO_2$). Such blood gas analyzers require frequent calibration and quality control checks to insure the analyzer is operating properly and accurately. In connection with such quality control and calibration procedures, it is convenient to use a prepared blood gas control liquid of constant, known composition to monitor the accuracy of such analyzers. Commercially available, prepared aqueous blood gas control liquids adequately mimic blood for pH and $pCO_2$, but do not have adequate oxygen buffering capacity as they are unable to dissolve an adequate amount of oxygen. Such controls are therefore prone to inaccuracy in the presence of relatively small amounts of outside oxygen contamination, and also may indicate certain types of instrument malfunctions which do not exist.

Other blood gas control products have been proposed which are based on components of human blood or stable fluorocarbon compound emulsions which are used as blood substitutes. Such fluorocarbon compound emulsions are able to take up considerably more oxygen than is water, and therefore have good oxygen buffer capacities, the partial pressure of oxygen in the liquid being less subject to influence by the loss or gain of oxygen which can occur during use. One such blood gas control product is described in Sorenson et al. U.S. Pat. No. 4,163,734. The blood gas control product there proposed contains a perfluorotributylamine compound, an emulsifying agent to provide a stable suspension of the perfluorinated compound, a phosphate buffer system, and a bicarbonate ion-carbon dioxide buffer system. Sterilization, which is necessary for stability, is accomplished by means of radioactive irradiation.

Such a control liquid has several undesirable limitations. The oxygen solubility constant of perfluorotributylamine, although higher than that of water, nonetheless requires a high fluorocarbon:water ratio which results in an undesirably high viscosity that is much higher than that of blood. The emulsion leaves bubbles in the measuring chambers of blood gas analyzer equipment, creating cleaning difficulties and causing control-to-sample carry over. The specific surfactant described in Sorenson et al., like all polyol surfactants, must be used in an amount that further undesirably increases viscosity. Also the phosphate buffer system is conductive to growth of aerobic bacteria, which impair $pO_2$ stability, and efforts to sterilize the product by means of radioactive irradiation are themselves detrimental to oxygen stability. Countering the problem with an aldehydic preservative such as formaldehyde would not be possible because such preservatives react with phosphates, rendering both the buffer and the preservative ineffective.

We have discovered that a superior blood gas control liquid can be produced by employing a perfluorinated compound material with a high enough $O_2$ solubility constant such that a smaller percent oil in water emulsion yields acceptable oxygen buffer capacity, while maintaining a viscosity in the range of blood. This perfluorinated liquid is used in conjunction with a non-ionic fluorocarbon-based surfactant, a preservative for inhibiting microbial growth, and a buffering agent substantially non-reactive with the preservative. The liquids of the invention have superior oxygen buffering capacity, good pH buffering, and viscosity comparable to that of blood. In addition, they discourage microbial growth without the use of irradiation or expensive sterile fill procedures. Further, they do not foam or form bubbles to a significant degree and are easily cleaned out of blood gas measuring equipment.

Accordingly, the blood gas control liquid of the invention, which is preferably supplied enclosed in gas-tight, sealed ampuls, contains known concentrations of dissolved carbon dioxide and oxygen. The liquid is a water-based emulsion containing a water-insoluble perfluorinated compound material, a fluorocarbon-based surfactant capable of emulsifying the perfluorinated compound material, a preservative in a concentration sufficient to inhibit microbial growth without interfering with the quality control functions of the liquid, and a buffering agent substantially non-reactive with said preservative.

According to the invention, the perfluorinated compound material must have a high enough oxygen solubility coefficient, and be present in sufficient quantity, to yield a blood gas control liquid having an effective oxygen solubility coefficient of at least 10 ml $O_2$/100 ml of emulsion. Further, the perfluorinated compound material must have a high enough oxygen solubility coefficient to allow it to be used in an amount which constitutes less than about 40% of the liquid by volume, because larger volumetric amounts would raise viscosity to an unacceptable level. To provide a margin of safety, the effective oxygen coefficient of the perfluorinated compound material used in the invention should be, at one atmosphere pressure, 25° C., and a volumetric proportion of 15%, at least 10 mL $O_2$/100 mL emulsion.

A preferred perfluorinated compound material of the invention is manufactured by 3M Company under the designation "FC-77" and is a mixture of perfluoroalkanes and perfluorocyclic ethers. We have found that FC-77 may be advantageously used in combination with perfluorotributylamine, sold by 3M Company under the designation "FC-43". These perfluorinated compound materials have the oxygen solubility coefficients shown in Table I below. The preferred fluorocarbon-based surfactants of the invention include fluoroalkylpoly(ethyleneoxy)ethanol, sold by DuPont Corporation under the designation Zonyl FSN; fluoracylpolyoxyethylene, sold under the designation Lodyne S-107 by Ciba-Geigy; fluorinated acylpolyoxyethylene ethanol, sold under the designation FC-170-C by 3M Company; and Monflor 51, a polymer of about 20–25 units of polyethyleneoxide with between one and four tetrafluoroethylene groups at each end, sold by Imperial Chemical Industries Ltd.

TABLE I

| VOLUME SOLUBILITY IN ml $O_2$ per ml EMULSION (at one atmosphere and 25° C.) | | | |
|---|---|---|---|
| | % Fluorocarbon Oil in Water | | |
| | 10% | 15% | 20% |
| FC-43 | 6.12 | 7.78 | 9.44 |
| FC-77 | 8.12 | 10.78 | 13.44 |
| FC-77/FC-43 | 7.62 | 10.03 | 12.44 |

The buffering agent used in the invention is selected so that it is substantially non-reactive with the preservative being used. Because the preferred preservatives are the aldehydes, and particularly formaldehyde and guteraldehyde, the preferred buffering agents are those containing a tertiary amine; such buffering agents do not react with aldehydes, and also are relatively non-conductive to microbial growth. The preferred tertiary amine buffering agent for use with an aldehydic preservative is HEPES (N-2-Hydroxyethyl-piperazine-N'-2-ethane sulfonic acid), its pK being centered in the appropriate physiological pH range. Another effective tertiary amine buffering agent for use with adlehydic preservatives is triethanolamine.

The most preferred embodiment of the invention has the following formulation:

| Compound | Concentration |
| --- | --- |
| FC-77 | 15% (v/v) |
| FC-43 | 5% (v/v) |
| Fluoroalkyl poly (ethyleneoxy) ethanol (Zonyl FSN) | 2% (v/v) |
| HEPES Buffer salts | 40 mM |
| NaOH | 38.7–42.57 mM |
| NaCl | 85.47–89.29 mM |
| Formaldehyde | 53 mM |

The first step in the preparation of the preferred liquid was to prepare the antibacterial surfactant/water solution by mixing together 500 grams of 40% Zonyl FSN and 60 mL of formaldehyde and bringing the solution up to 8.0 liters with distilled water. Next, an oil mixture was prepared by combining 1.5 L FC-77 with 0.5 L FC-43.

The aqueous solution was placed in the hopper of a Gaulin Homogenizer (Model 15M) and the oil mixture placed in a separatory funnel mounted above the hopper. Oil was dripped into the hopper at the rate of 100 mL/min. while the liquid in the hopper was homogenized at a pressure of 2500 psi. The liquid was repeatedly passed through an ice bath and recirculated to the hoppper until all of the oil had been dripped into it. At this point, the pressure was increased to 8000 psi and nine discrete passes through the homogenizer were carried out. A stable emulsion was formed by the ninth pass.

The emulsion was allowed to stand for 24 hours, and was then filtered through Whatman #3 filter paper using vacuum filtration with a Buchner funnel.

In a separate operation, buffer solutions were prepared to be added to the emulsion. Three different buffer solutions were made using HEPES, NaOH, and NaCl in different concentrations. After the buffer solutions were added to the emulsions, each of the three emulsions was equilibrated with a different gas mixture, producing three different control liquids to be used under appropriate conditions. The three levels differed in pH, $pCO_2$, and $PO_2$, the levels having been chosen to reflect pH and gas partial pressure of the blood of normal patients, patients suffering from alkemia, and those suffering from acidemia. The three levels were:

| | Acidosis | Normal | Alkalosis |
| --- | --- | --- | --- |
| pH | 7.15–7.25 | 7.34–7.41 | 7.55–7.65 |
| $pCO_2$ | 65–75 mm Hg | 40–47 mm Hg | 18–24 mm Hg |
| $pO_2$ | 60–70 mm Hg | 95–110 mm Hg | 140–160 mm Hg |

The buffer formulations corresponding to the three levels where:

| | Acidosis | Normal | Alkalosis |
| --- | --- | --- | --- |
| NaOH | 38.7mM/L emulsion | 40.62 mM/L | 42.57 mM/L |
| HEPES | 40.00 mM | 40.00 mM/L | 40.00 mM/L |
| NaCl | 89.29 mM | 87.38 mM/L | 85.43 mM/L |

The buffer formulations were added to the emulsion and each level was then given a distinctive color using the following dyes:

| Acidosis | Normal | Alkalosis |
| --- | --- | --- |
| 100 mg/l Yellow #5 | 100 mg/l Amarath | 66.67 mg/l Amarath, 133.33 mg/l Yellow #5 |

The emulsions, containing dyes and dissolved buffer salts and having viscosities comparable to blood, were then placed in a container which was thermally controlled to 25° C. ±0.5° C. The appropriate equilibration gas mixture was then bubbled through each emulsion at the rate of 2 mL/min. until the pH, $pO_2$, and $pCO_2$ reached equilibrium values, as determined by blood gas measuring equipment. The equilibration gas mixtures had the following compositions:

| | Acidosis | Normal | Alkalosis |
| --- | --- | --- | --- |
| $CO_2$ | 7.0% | 4.17 | 1.98 |
| $O_2$ | 9.5% | 14.0 | 21.5 |
| $N_2$ | 83.5% | 81.83 | 76.52 |

After equilibration, glass ampuls which had been purged with the same gas equilibration mixture used for the emulsion were filled with 1 mL of the appropriate emulsion, up to below a hand-breakable line, and the ampuls heat-sealed.

Another embodiment of the invention employs a mixture of perfluoroalkanes and perfluorocyclic ethers (FC-77) and a polymer of about 20–25 units of polyethyleneoxide with between one and four tetrafluoroethylene groups at each end (Monflor 51). Two liters of FC-77 were emulsified, as described above for the FC-77/FC-43 emulsion, with an antibacterial surfactant/water solution consisting of 150 g Monflor 51 (about 1.5% by volume of emulsion) and 60 ml formaldehyde brought up to 8.00 liters with distilled water. After all the FC-77 had been added, the emulsion was subjected to seven discrete passes through the Gaulin Homogenizer.

Because Monflor 51 often contains HF as an impurity, the emulsions were neutralized with NaOH. After neutralization, buffers and dyes were added as described above for FC-77/FC-43, they were equilibrated with the appropriate gas mixtures, and the emulsions placed in ampuls.

The embodiments described above do not include added bicarbonate, but these emulsions nevertheless, owing to the gas equilibration step, effectively contain bicarbonate. Alternatively, it is of course possible to add bicarbonate, in appropriate amounts, along with HEPES.

The emulsions, in their sealed ampuls, were used successfully to check the calibration of blood gas analyzers. An ampul containing the appropriate emulsion is opened and the control liquid is placed in the blood gas analyzer, which measures and registers the pH, $pCO_2$ and $pO_2$ of the emulsion. A reading outside of the pH and gas partial pressure ranges known to exist in the liquid indicates the need for re-calibration or repair of the analyzer.

We claim:

1. A blood gas control product comprising a sealed container and a liquid composition of matter in said container, said composition of matter comprising
   water,
   5–40% by volume of a water-insoluble perfluorinated compound material, said perfluorinated compound material having an oxygen solubility coefficient, at one atmosphere pressure, 25° C., and a volumetric proportion of 15%, of at least 10 ml $O_2$ per 100 ml liquid,
   0.25–10% by volume of a non-ionic fluorocarbon-based surfactant capable of emulsifying said perfluorinated compound material,
   a preservative present in a concentration sufficient to inhibit microbial growth in said blood gas control liquid without impairing the quality control functions of said liquid, and
   a pH buffering agent substantially non-reactive with said preservative, said blood gas control liquid having a pH in the range of 7.0 to 8.0, a partial pressure of $CO_2$ in the range of 15–80 mm Hg, and a partial pressure of $O_2$ in the range of 20–600 mm Hg.

2. The blood gas control product of claim 1 wherein said preservative is an aldehyde, and
   said buffering agent includes a tertiary amine.

3. The blood gas control product of claim 2 wherein said aldehyde is formaldehyde, and
   said tertiary amine is HEPES.

4. The product of claim 1 wherein said composition further includes a coloring agent selected from the class consisting of Yellow #5 and Amarath, and a mixture thereof.

5. The product of claim 1 wherein the viscosity of said composition is comparable to blood.

6. The product of claim 1 wherein said composition contains less than 25% by volume of said compound material, less than 5% by volume of said surfactant, said preservative includes an aldehyde, said buffering agent includes a tertiary amine, and partial pressure of oxygen in the range of 50–80 mm Hg, and said composition further includes a coloring agent selected from the class consisting of Yellow #5 and Amarath, and a mixture thereof.

7. The blood gas control product of claim 3, wherein said compound material comprises a mixture of perfluoroalkanes, perfluorocyclic ethers, and perfluorotributylamine, and
   said non-ionic fluorocarbon-based surfactant comprises fluoroalkylpoly(ethyleneoxy)ethanols.

8. The blood gas control product of claim 3, wherein said compound material comprises a mixture of perfluoroalkanes and perfluorocyclic ethers, and
   said non-ionic fluorocarbon-based surfactant comprises a polymer of about 20–25 units of polyethylene oxide with between one and four tetrafluoroethylene groups at each end.

9. The blood gas control product of claim 7 wherein said perfluoroalkanes and perfluorocyclic ethers togehter comprise about 15% by volume of said liquid,
   said perfluorotributyl amine comprises about 5% by volume of said liquid,
   said fluoroalkylpoly(etheleneoxy)ethanol comprises about 2% by volume of said liquid,
   said preservative is formaldehyde present in a concentration of about 53 mM, and
   said product further comprises at least one dye.

10. The blood gas control product of claim 8 wherein said perfluoroalkanes and perfluorocyclic ethers together comprise about 20% of said liquid,
    said non-ionic polymeric, fluorocarbon-based surfactant comprises about 2% of said liquid by volume, and
    said preservative is formaldehyde present in a concentration of about 53 mM, and
    said product further comprises at least one dye.

* * * * *

UNITED STATES PATENT AND TRADEMARK OFFICE
CERTIFICATE OF CORRECTION

PATENT NO. : 4,299,728

DATED : November 10, 1981

INVENTOR(S) : Alan D. Cormier, et al.

It is certified that error appears in the above-identified patent and that said Letters Patent are hereby corrected as shown below:

Column 1, line 54-55 "conductive" should be --conducive--.

Column 4, line 31 "mL/min." should be --L/min.--.

Signed and Sealed this

Sixteenth Day of February 1982

[SEAL]

Attest:

GERALD J. MOSSINGHOFF

Attesting Officer

Commissioner of Patents and Trademarks